United States Patent
Nakamura et al.

(10) Patent No.: US 7,348,329 B2
(45) Date of Patent: Mar. 25, 2008

(54) THERAPEUTIC AGENT FOR KERATOCONJUNCTIVAL DISORDER

(75) Inventors: Masatsugu Nakamura, Ikoma (JP); Shin-ichiro Hirai, Ikoma (JP)

(73) Assignee: Santen Pharmaceutical Co., Ltd., Osaka-shi, Osaka (JP)

( * ) Notice: Subject to any disclaimer, the term of this patent is extended or adjusted under 35 U.S.C. 154(b) by 141 days.

(21) Appl. No.: 10/576,402

(22) PCT Filed: Oct. 29, 2004

(86) PCT No.: PCT/JP2004/016460

§ 371 (c)(1),
(2), (4) Date: Apr. 20, 2006

(87) PCT Pub. No.: WO2005/039571

PCT Pub. Date: May 6, 2005

(65) Prior Publication Data

US 2007/0093514 A1   Apr. 26, 2007

(30) Foreign Application Priority Data

Oct. 29, 2003 (JP) .............................. 2003-368548
Nov. 10, 2003 (JP) .............................. 2003-379801

(51) Int. Cl.
A61K 31/425 (2006.01)
A61K 31/505 (2006.01)

(52) U.S. Cl. ...................... 514/259; 514/256; 514/267; 514/269

(58) Field of Classification Search ................. 514/259, 514/256
See application file for complete search history.

(56) References Cited

U.S. PATENT DOCUMENTS

| | | |
|---|---|---|
| 5,447,946 A | 9/1995 | Kuronu et al. |
| 5,885,997 A | 3/1999 | Lohray et al. |
| 5,886,014 A | 3/1999 | Fujita et al. |
| 6,372,750 B2 * | 4/2002 | Lohray et al. ............ 514/266.2 |
| 6,573,268 B1 | 6/2003 | Lohray et al. |
| 6,780,992 B2 | 8/2004 | Lohray et al. |

2007/0060628 A1   3/2007   Nakamura et al.

FOREIGN PATENT DOCUMENTS

| | | |
|---|---|---|
| JP | 3-72227 B2 | 11/1991 |
| JP | 8-231549 A | 9/1996 |
| JP | 9-295970 A | 11/1997 |
| JP | 11-130675 A | 5/1999 |
| JP | 2001-39976 A | 2/2001 |
| JP | 2002-515874 A | 5/2002 |
| JP | 2002-220336 A | 8/2002 |
| JP | 2002-255854 A | 9/2002 |
| JP | 2003-509503 A | 3/2003 |
| WO | WO 97/41097 A | 11/1997 |
| WO | WO 01/21602 A1 | 3/2001 |

OTHER PUBLICATIONS

Hisashi Hosoya (Hisashi Hosotani), "Tonyobyosei Kakumakusho", "Diabetic Kerathopathy", *The Journal of the Eye*, 1996, 13(6), pp. 845-851.
Kazuko Kameyama, "Tonyobyo Gappeisho to Shiteno Ganbyohen", *Clinics & Drug Therapy*, 2002, 21(11), pp. 1089 to 1092.
Yasuichiro Chikama, "Hen'ensei Kakumaku Johi Kasson", "Diagnosis and Medical Treatment for Persistent Epithelial Defect", Ganka, 2001, 43, pp. 1625 to 1631.
*Japanese Review of Clinical Ophthalmology*, 46, 738-743 (1992).
Chikako Katakami, "A New Treatment for Corneal Epithelial Defects Using Fibronectin, EGF and Hyaluronic Acid", *Ophthalmic Surgery*, 5, 719-727 (1992).
U.S. Appl. No. 10/576,719 filed Apr. 20, 2006; Group Art Unit 1614; Confirmation No. 6306.

* cited by examiner

*Primary Examiner*—Michael G. Hartley
*Assistant Examiner*—Jagadishwar Samala
(74) *Attorney, Agent, or Firm*—Frishauf, Holtz, Goodman & Chick, P.C.

(57) ABSTRACT

An object of the present invention is to discover a new medicinal use of 5-[4-[[3-methyl-4-oxo-3,4-dihydro-2-quinazolinyl]methoxy]phenylmethyl]thiazolidine-2,4-dione and N-[(4-methoxyphenoxy)carbonyl]-N-[[4-[2-(5-methyl-2-phenyl-4-oxazolyl)ethoxy]phenyl]methyl]glycine. Both of the compounds exert an excellent improving effect on corneal disorder models and is useful as a therapeutic agent for a keratoconjunctival disorder such as dry eyes, corneal ulcer, keratitis, conjunctivitis, superficial punctate keratopathy, corneal epithelial defects, conjunctive epithelial defects, keratoconjunctivitis sicca, superior limbic keratoconjunctivitis and filamentary keratitis.

5 Claims, No Drawings

THERAPEUTIC AGENT FOR KERATOCONJUNCTIVAL DISORDER

This application is the United States national phase application of International Application PCT/JP2004/016460 filed Oct. 29, 2004.

TECHNICAL FIELD

The present invention relates to a therapeutic agent for a keratoconjunctival disorder such as dry eyes, corneal ulcer, keratitis, conjunctivitis, superficial punctate keratopathy, corneal epithelial defects, conjunctive epithelial defects, keratoconjunctivitis sicca, superior limbic keratoconjunctivitis and filamentary keratitis, comprising as an active ingredient, 5-[4-[[3-methyl-4-oxo-3,4-dihydro-2-quinazolinyl]methoxy]phenylmethyl]thiazolidine-2,4-dione, N-[(4-methoxyphenoxy)carbonyl]-N-[[4-[2-(5-methyl-2-phenyl-4-oxazolyl)ethoxy]phenyl]methyl]glycine, or a salt thereof.

BACKGROUND ART

Cornea is a transparent avascular tissue having a diameter of about 1 cm and a thickness of about 1 mm, while conjunctiva is a mucosal membrane covering the eyeball surface posterior to the corneal margin, and the back face of the eyelid. The cornea and the conjunctiva are known to significantly affect the visual function. Keratoconjunctival disorders caused due to a variety of diseases such as corneal ulcer, keratitis, conjunctivitis, dry eyes and the like may adversely affect normal architecture of epithelium, and furthermore, may impair structures and functions of the stroma and endothelium, when the repair of these disorders are retarded, alternatively when these disorders are prolonged without making repair on some grounds. That is because the cornea and the conjunctiva are connected tissues. In these years, with the development of cell biology, factors participating in cell proliferation, migration, adhesion, extension, differentiation and the like had been elucidated, and it was reported that these factors play important roles in repair of corneal disorders (Japanese Review of Clinical Ophthalmology, 46, 738-743 (1992), Ophthalmic Surgery, 5, 719-727 (1992)).

JP-T-2002-515874 describes the invention which relates to a heterocyclic compound and discloses that an azolidinedione derivative such as 5-[4-[[3-methyl-4-oxo-3,4-dihydro-2-quinazolinyl]methoxy]phenylmethyl]thiazolidine-2,4-dione or a sodium salt thereof is effective as a therapeutic agent for a disease caused by insulin resistance such as type II diabetes or dyslipidemia, a cardiovascular disorders such as hypertension and a coronary heart disease. JP-T-2003-509503 describes the invention which relates to a substituted acid derivative which is useful as an anti-diabetes agent and an anti-obesity agent and discloses that a compound such as N-[(4-methoxyphenoxy)carbonyl]-N-[[4-[2-(5-methyl-2-phenyl-4-oxazolyl)ethoxy]phenyl]methyl]glycine is effective as a therapeutic agent for disease such as diabetes (particularly type II diabetes), hyperglycemia, hyperinsulinism, hyperlipemia or obesity. JP-A-2002-255854 describes the invention which relates to a pharmaceutical composition obtained by combining a diuretic and an insulin resistance improving agent and is characterized by suppressing an increase in heart weight, cardiac enlargement, the development of edema or fluid retention which is generally known as a side effect of an insulin resistance improving agent by the concomitant use of a diuretic, and discloses N-[(4-methoxyphenoxy)carbonyl]-N-[[4-[2-(5-methyl-2-phenyl-4-oxazolyl)ethoxy]phenyl]methyl]glycine as one of the insulin resistance improving agents.

However, there has been no report in which a pharmacological effect of these compounds on an eye disease such as a keratoconjunctival disorder is studied.

DISCLOSURE OF THE INVENTION

It is an interesting subject to discover a new medicinal use of 5-[4-[[3-methyl-4-oxo-3,4-dihydro-2-quinazolinyl]methoxy]phenylmethyl]thiazolidine-2,4-dione and N-[(4-methoxyphenoxy)carbonyl]-N-[[4-[2-(5-methyl-2-phenyl-4-oxazolyl)ethoxy]phenyl]methyl]glycine.

The present inventors have made intensive studies in order to discover a new medicinal use of the above-mentioned compounds, and as a result, they found that both of these compounds exert an excellent improving effect on a corneal damages in a test for therapeutic effect using corneal disorder models and thus the present invention has been completed.

That is, the present invention is directed to a therapeutic agent for a keratoconjunctival disorder such as dry eyes, corneal ulcer, keratitis, conjunctivitis, superficial punctate keratopathy, corneal epithelial defects, conjunctive epithelial defects, keratoconjunctivitis sicca, superior limbic keratoconjunctivitis and filamentary keratitis comprising as an active ingredient 5-[4-[[3-methyl-4-oxo-3,4-dihydro-2-quinazolinyl]methoxy]phenylmethyl]thiazolidine-2,4-dione, N-[(4-methoxyphenoxy)carbonyl]-N-[[4-[2-(5-methyl-2-phenyl-4-oxazolyl)ethoxy]phenyl]methyl]glycine or a salt thereof (hereinafter, these are referred to as "the present compounds").

The salt of 5-[4-[[3-methyl-4-oxo-3,4-dihydro-2-quinazolinyl]methoxy]phenylmethyl]thiazolidine-2,4-dione or N-[(4-methoxyphenoxy)carbonyl]-N-[[4-[2-(5-methyl-2-phenyl-4-oxazolyl)ethoxy]phenyl]methyl]glycine is not particularly limited as long as it is a pharmaceutically acceptable salt. Examples thereof include sodium salts, potassium salts, lithium salts, calcium salts, magnesium salts, salts with an inorganic acid such as hydrochloric acid, nitric acid or sulfuric acid, salts with an organic acid such as acetic acid, fumaric acid, maleic acid, succinic acid or tartaric acid, and the like. Quaternary ammonium salts are also included in the salt according to the present invention. Preferred salts are sodium salts and potassium salts. The present compounds may be in a form of a hydrate or a solvate. A geometric isomer, optical isomer, tautomer or polymorphism of any of the present compounds may also be included in the scope of the present invention.

The keratoconjunctival disorder referred to herein means the state of damaged cornea and/or conjunctiva due to various factors, and examples thereof include dry eyes, corneal ulcer, keratitis, conjunctivitis, superficial punctate keratopathy, corneal epithelial defects, conjunctive epithelial defects, keratoconjunctivitis sicca, superior limbic keratoconjunctivitis, filamentary keratitis and the like.

The therapeutic agent for a keratoconjunctival disorder of the invention may be administered either orally or parenterally. Examples of the dosage form include eye drops, ophthalmic ointments, injections, tablets, capsules, granules, powders and the like. In particular, eye drops are preferred. These can be prepared using any of generally used techniques. For example, the eye drops can be prepared using a tonisity agent such as sodium chloride or concentrated glycerin, a buffer such as sodium phosphate or sodium acetate, a surfactant such as polyoxyethylene sorbitan monooleate, polyoxyl 40 stearate or polyoxyethylene hardened castor oil, a stabilizer such as sodium citrate or sodium edetate, a preservative such as benzalkonium chloride or paraben as needed. The pH is permitted as long as it falls within the range that is acceptable as an ophthalmic preparation, but is preferably in the range of from 4 to 8.

The ophthalmic ointment can be prepared with a generally used base such as white soft paraffin or liquid paraffin. Also, oral preparations such as tablets, capsules, granules and powders can be prepared by adding an expander such as lactose, crystalline cellulose, starch or vegetable oil, a lubricant such as magnesium stearate or talc, a binder such as hydroxypropyl cellulose or polyvinyl pyrrolidone, a disintegrant such as carboxymethyl cellulose calcium or low-substituted hydroxypropylmethyl cellulose, a coating agent such as hydroxypropylmethyl cellulose, macrogol or a silicon resin, a film forming agent such as gelatin film, and the like, as needed.

The present invention also relates to a method for treating a keratoconjunctival disorder comprising administering to a patient, 5-[4-[[3-methyl-4-oxo-3,4-dihydro-2-quinazolinyl]methoxy]phenylmethyl]thiazolidine-2,4-dione, N-[(4-methoxyphenoxy)carbonyl]-N-[[4-[2-(5-methyl-2-phenyl-4-oxazolyl)ethoxy]phenyl]methyl]glycine or a salt thereof in a therapeutically effective amount.

The dose can properly be selected depending on the symptoms, age, dosage form and the like. In the case of an eye drop, it may be instilled once to several times a day at a concentration of from 0.0001 to 5% (w/v), preferably from 0.001 to 3% (w/v). In the case of an oral preparation, it may be administered once or divided into several times at a dose of generally from 0.1 to 5000 mg per day, preferably from 1 to 1000 mg per day.

As will be described below, when a test for a therapeutic effect on a corneal damage was carried out, any of the present compounds were found to exert an excellent improving effect on corneal disorder models. Therefore they are useful as a therapeutic agent for a keratoconjunctival disorder such as dry eyes, corneal ulcer, keratitis, conjunctivitis, superficial punctate keratopathy, corneal epithelial defects, conjunctive epithelial defects, keratoconjunctivitis sicca, superior limbic keratoconjunctivitis and filamentary keratitis.

BEST MODE FOR CARRYING OUT THE INVENTION

Hereinafter, results of a pharmacological test and preparation examples using the present compounds will be shown, however, these examples are for understanding the invention well, and are not meant to limit the scope of the invention.

Pharmacological Test

Test for Therapeutic Effect on Corneal Damage

Using male SD rats, in accordance with the method of Fujihara et al. (Invest. Ophthalmol. Vis. Sci. 42 (1): 96-100 (2001)), corneal disorder models were produced. After the production of the corneal disorder models, the improvement ratio of a corneal damage was evaluated according to the method of Murakami et al. (journal of the eye 21 (1): 87-90 (2004))

(Test Method)

A male SD rat was systemically anesthetized by an administration of Nembutal. Subsequently the exorbital lacrimal gland was removed and a corneal damage was induced over a period of 2 months.

Then, 5-[4-[[3-methyl-4-oxo-3,4-dihydro-2-quinazolinyl]methoxy]phenylmethyl]thiazolidine-2,4-dione (Compound A) or N-[(4-methoxyphenoxy)carbonyl]-N-[[4-[2-(5-methyl-2-phenyl-4-oxazolyl)ethoxy]phenyl]methyl]glycine (Compound B) was administered as follows.

Compound A Administered Group:

A physiological saline solution of Compound A (0.02%) was instilled into both eyes 6 times a day for 7 days (one group consisting of 4 animals, 8 eyes).

Compound B Administered Group:

A physiological saline solution of Compound B (0.02%) was instilled into both eyes 6 times a day for 7 days (one group consisting of 4 animals, 8 eyes).

In a control group, physiological saline was instilled into both eyes 6 times a day for 7 days (one group consisting of 4 animals, 8 eyes).

Seven days after the start of instillation, the damaged parts of the cornea were stained with fluorescein. For each of the upper, middle and lower parts of the cornea, the degree of fluorescein staining was evaluated by scoring according to the criteria shown below and the mean value of the total scores for each of the above-mentioned parts was calculated.

Further, the mean value of the total scores for the normal eye was also calculated.

(Evaluation Criteria)

0: No punctate staining
1: Scattered staining (punctate, separated staining)
2: Moderate staining(a part of punctate staining being adjacent)
3: Heavy staining (punctate, barely separated staining)

(Results)

By taking the mean value of the total scores for the control group (physiological saline) as a reference (improvement ratio: 0%), the calculation was carried out according to the calculation formula shown below. Each of the improvement ratios for the Compound A administered group and the Compound B administered group are shown in Table 1 and Table 2. The mean value of the scores is a mean of those of 8 cases, respectively.

Improvement ratio (%)={(control)−(the present compound)}/damage degree×100

Damage degree=(control)−(normal eye)

TABLE 1

| Group | Mean value of total scores | Improvement ratio (%) |
|---|---|---|
| Normal eye | 3.3 | |
| Control group | 5.8 | 0 |
| Compound A administered group | 4.8 | 40.0 |

TABLE 2

| Group | Mean value of total scores | Improvement ratio (%) |
|---|---|---|
| Normal eye | 3.7 | |
| Control group | 6.3 | 0 |
| Compound B administered group | 5.2 | 42.3 |

(Discussion)

As apparent from the results of the above pharmacological test using rats (Table 1 and Table 2), both Compound A and Compound B significantly improve a corneal damage.

FORMULATION EXAMPLES

Hereinafter, representative formulation examples using Compound A or Compound B will be shown.

Formulation Example 1

In 100 ml,

| | |
|---|---|
| Compound A | 10 mg |
| Sodium Chloride | 900 mg |
| Sterile purified water | q.s. |

By altering the amount of Compound A to be added, an eye drop at a concentration of 0.001% (w/v), 0.03% (w/v), 0.1% (w/v), 0.3% (w/v), 1.0% (w/v), or 3.0% (w/v) can be prepared.

Formulation Example 2

In 100 ml,

| | |
|---|---|
| Compound B | 100 mg |
| Sodium Chloride | 800 mg |
| Disodium hydrogen phosphate | 100 mg |
| Sodium dihydrogen phosphate | q.s. |
| Sterile purified water | q.s. |

By altering the amount of Compound B to be added, an eye drop at a concentration of 0.01% (w/v), 0.3% (w/v), 0.5% (w/v), 1.5% (w/v), or 3% (w/v) can be prepared.

Formulation Example 3

In 100 g,

| | |
|---|---|
| Compound A | 0.3 g |
| Liquid paraffin | 10.0 g |
| white soft paraffin | q.s. |

By altering the amount of Compound A to be added, an ophthalmic ointment at a concentration of 1% (w/w) or 3% (w/w) can be prepared.

Formulation Example 4

In 100 g,

| | |
|---|---|
| Compound B | 0.3 g |
| Liquid paraffin | 10.0 g |
| white soft paraffin | q.s. |

By altering the amount of Compound B to be added, an ophthalmic ointment at a concentration of 1% (w/w) or 3% (w/w) can be prepared.

INDUSTRIAL APPLICABILITY

Both 5-[4-[[3-methyl-4-oxo-3,4-dihydro-2-quinazolinyl]methoxy]phenylmethyl]thiazolidine-2,4-dione and N-[(4-methoxyphenoxy)carbonyl]-N-[(4-[2-(5-methyl-2-phenyl-4-oxazolyl)ethoxy]phenyl]methyl]glycine exert an excellent improving effect on a corneal damage.

The invention claimed is:

1. A method for treating a keratoconjunctival disorder comprising administering to a patient in need thereof a therapeutically effective amount of a compound selected from the group consisting of
   (i) 5- [4- [[3-methyl-4-oxo-3,4-dihydro-2-quinazolinyl] methoxy]phenylmethyl]thiazolidine-2,4-dione or a pharmaceutically acceptable salt thereof, and
   (ii) N-[(4-methoxyphenoxy)carbonyl]-N-[[4-[2-(5-methyl-2-phenyl-4-oxazolyl) ethoxy]phenyl]methyl]glycine or a pharmaceutically acceptable salt thereof.

2. The method according to claim 1, wherein the keratoconjunctival disorder is dry eyes, corneal ulcer, keratitis, conjunctivitis, superficial punctate keratopathy, corneal epithelial defects, conjunctive epithelial defects, keratoconjunctivitis sicca, superior limbic keratoconjunctivitis or filamentary keratitis.

3. The method according to claim 1, wherein the administration is instillation of an eye drop or administration of an ophthalmic ointment.

4. The method according to claim 1, wherein the compound is 5-[4-[[3-methyl-4-oxo-3,4-dihydro-2-quinazolinyl]methoxy] phenylmethyl]thiazolidine-2, 4-dione or a pharmaceutically acceptable salt thereof.

5. The method according to claim 1, wherein the compound is N-[(4-methoxyphenoxy) carbonyl]-N-[[4-[2-(5-methyl 2-phenyl-4-oxazolyl)ethoxyl]phenyl]methyl]glycine or a pharmaceutically acceptable salt thereof.

* * * * *